US011931329B2

(12) United States Patent
Hoffman et al.

(10) Patent No.: US 11,931,329 B2
(45) Date of Patent: Mar. 19, 2024

(54) COMPOSITIONS AND METHODS FOR TREATING ANXIETY-RELATED DISORDERS

(71) Applicant: Yamo Pharmaceuticals LLC, New York, NY (US)

(72) Inventors: Steven Hoffman, Mahwah, NJ (US); John Rothman, Lebanon, NJ (US)

(73) Assignee: YAMO PHARMACEUTICALS LLC, New York, NY (US)

( * ) Notice: Subject to any disclaimer, the term of this patent is extended or adjusted under 35 U.S.C. 154(b) by 0 days.

(21) Appl. No.: 17/817,543

(22) Filed: Aug. 4, 2022

(65) Prior Publication Data

US 2023/0040681 A1 Feb. 9, 2023

Related U.S. Application Data

(63) Continuation of application No. 16/778,334, filed on Jan. 31, 2020, now Pat. No. 11,446,268.

(60) Provisional application No. 62/800,016, filed on Feb. 1, 2019.

(51) Int. Cl.
| | | |
|---|---|---|
| A61P 25/22 | (2006.01) | |
| A61K 9/00 | (2006.01) | |
| A61K 9/20 | (2006.01) | |
| A61K 31/192 | (2006.01) | |
| A61K 31/195 | (2006.01) | |
| A61K 31/197 | (2006.01) | |
| A61K 31/198 | (2006.01) | |
| A61K 31/4045 | (2006.01) | |
| A61K 38/095 | (2019.01) | |
| A61K 45/06 | (2006.01) | |

(52) U.S. Cl.
CPC .......... *A61K 31/198* (2013.01); *A61K 9/0053* (2013.01); *A61K 31/197* (2013.01); *A61K 31/4045* (2013.01); *A61K 38/095* (2019.01); *A61K 45/06* (2013.01); *A61P 25/22* (2018.01)

(58) Field of Classification Search
CPC .. A61K 31/198; A61K 9/0053; A61K 31/197; A61K 31/4045; A61K 38/095; A61K 45/06; A61P 25/22
See application file for complete search history.

(56) References Cited

U.S. PATENT DOCUMENTS

| | | |
|---|---|---|
| 4,165,382 A | 8/1979 | Pozuelo |
| 2001/0047010 A1 | 11/2001 | Pozuelo |
| 2012/0322682 A1 | 12/2012 | McDevitt et al. |
| 2014/0073562 A1 | 3/2014 | Djupesland |
| 2015/0216827 A1 | 8/2015 | Hoffman |
| 2019/0015365 A1 | 1/2019 | Hoffman et al. |

FOREIGN PATENT DOCUMENTS

| | | |
|---|---|---|
| CA | 2601794 A1 | 10/2006 |
| CA | 3069703 A1 | 1/2019 |

OTHER PUBLICATIONS

Bareggi et al., "The use of escitalopram beyond major depression: pharmacological aspects, efficacy and tolerability in anxiety disorders," Exp Opin Drug MetabToxicol 3:741-753 (2007) (Year: 2007).*
MacNeil et al., "Anxiety in children and adolescents with Autism Spectrum Disorders," Res Autism Spectrum Disord 3:1-21 (2009) (Year: 2009).*
Andrisano et al., "Newer antidepressants and panic disorder: a meta-analysis," International Clinical Psychopharmacology 28:33-45 (2013) (Year: 2013).
Metyrosine, ChemSpider, accessed Nov. 6, 2021 at URL chemspider.com/Chemical-Structure.3013.html (Year: 2021).
Searcy "Pharmacological Prevention of Combat-Related Ptsd: A Literature Review," Military Medicine, 177, 6:649-654, 2012 (Year: 2012).
Maddox et al., Comorbid Social Anxiety Disorder in Adults with Autism Spectrum Disorder, J Autism Dev Disord 45:3949-3960 (2015) (Year: 2015).
Kewalramani, et al., "Asthma and Mood Disorders" Int. J. Child Health Hum. Dev., NIH Public Access, vol. 1, No. 2, 2008; pp. 115-123; p. 2, second paragraph; p. 7, second paragraph.
Davidson, et al., "Management of Generalized Anxiety Disorder in Primary Care: Identifying the Challenges and Unmet Needs" Prim. Care Companion J. Clin. Psychiatry, vol. 12, No. 2, 2010: 24 Pages, p. 10, second paragraph.
"What are the five major types of anxiety disorders?" Last reviewed on Feb. 12, 2014; Retrieved from https://www.nhs.gov/answers/mental-health-and-substance-abuse/what-are-the-five-major-types-of-anxiety-disorders/index.html; retrieved on Mar. 11, 2020; 2 Pages; p. 1. second paragraph; p. 2, second paragraph.
International Search Report and Written Opinion issued in PCT/US20/16086, dated Apr. 23, 2020.
International Patent Application No. PCT/US2020/016086; Int'l Preliminary Report on Patentability; dated Aug. 12, 2021; 8 pages.
Steensel et al.; "Anxiety Disorders in Children and Adolescents with Autistic Spectrum Disorders: A Meta-Analysis"; Clinical Child and Family Psychology Review; vol. 14, 2011; p. 302-317.
Anagnostou et al.; "4 drugs can improve autism's repetitive behaviors"; Current Psychiatry; vol. 5 No. 4: Apr. 2006; p. 55-64.
Spitzer et al.; "A Brief Measure for Assessing Generalized Anxiety Disorder—The GAD-7"; Arch Intern. Med.; vol. 166; May 2006; p. 1092-1097.
Osorio et al.; "Instruments for the assessment of social anxiety disorder: Validation studies"; World Journal of Psychiatry; vol. 2(5); Oct. 2012; p. 83-85.
Clayton P. Axelby; "Social Phobia: Etiology, Diagnosis and Treatment"; Nova Science Publishers Inc.; © 2009; 289 pages.

(Continued)

*Primary Examiner* — Julie Ha
*Assistant Examiner* — Kristina M Hellman
(74) *Attorney, Agent, or Firm* — BakerHostetler

(57) ABSTRACT

The present invention provides methods, compositions, and kits for treating anxiety-related disorders, including OCD and SAD, and for reducing anxiety, obsessive behavior, or compulsive behavior in subjects in need thereof.

20 Claims, No Drawings

(56) References Cited

OTHER PUBLICATIONS

European Patent Application No. 20748147.4; Extended Search Report; dated Sep. 26, 2022; 9 pages.
Longhurst et al.; "Effects of Catecholamine Depletion with AMPT (alpha-methyl-para-tyrosine) in Obsessive-Compulsive Disorder"; Biological Psychiatry; vol. 46; 1999; p. 573-576.

* cited by examiner

COMPOSITIONS AND METHODS FOR TREATING ANXIETY-RELATED DISORDERS

CROSS-REFERENCE TO RELATED APPLICATION

This application is a continuation of U.S. patent application Ser. No. 16/778,334, filed Jan. 31, 2020, which claims the benefit of priority to U.S. Provisional Patent Application No. 62/800,016 filed on Feb. 1, 2019. The entirety of each of the aforementioned applications is incorporated by reference herein.

TECHNICAL FIELD

The present inventions relate generally to compositions, kits, and methods for treating anxiety-related disorders, including obsessive-compulsive disorder (OCD) and Social Anxiety Disorder (SAD), and for reducing anxiety, obsessive behaviors, or compulsive behaviors in patients in need thereof.

BACKGROUND

Mental health disorders are generally diagnosed using criteria set forth in the American Psychiatric Association's Diagnostic and Statistical Manual (DSM). The fourth edition of DSM (DSM-IV) categorized OCD as an anxiety disorder, along with Generalized Anxiety Disorder (GAD), Panic Disorder, Post-traumatic Stress Disorder (PTSD), and Social Anxiety Disorder (SAD). The fifth edition of the DSM (DSM-V), however, removed OCD from the list of anxiety disorders and placed it within its own chapter.

Autism Spectrum Disorder ("ASD" or "autism"), is a developmental disorder characterized by social, communication, and behavioral difficulties. Individuals with ASD also often experience anxiety, and are frequently diagnosed with a co-morbid anxiety disorder. One study estimated that 40% of children with ASD also had at least one DSM-IV anxiety disorder (Specific Phobia: 30%; Obsessive-Compulsive Disorder: 17%; Social Anxiety Disorder/Agoraphobia: 17%; Generalized Anxiety Disorder: 15%; Separation Anxiety Disorder: 9%; Panic Disorder: 2%). See van Steensel et al., Anxiety Disorders in Children and Adolescents with Autistic Spectrum Disorders: A Meta-Analysis, Clin Child Fam Psychol Rev (2011) 14:302-317.

In addition, ASD is often comorbid with a variety of genetic disorders. For example, ASD rates are elevated in individuals with seizural disorders, schizophrenia, 22q deletion syndrome, Angelman syndrome, CHARGE syndrome, Cornelia de Lange syndrome, Down syndrome, Duchenne Muscular Dystrophy, Prader-Willi syndrome, Smith-Lemli-Opitz syndrome, Retts syndrome, Fragile X syndrome, Smith Magenis syndrome, Sotos syndrome, and Tuberous Sclerosis. See carautismroadmap.org/asd-and-other-genetic-conditions.

Obsessions and/or compulsions are the primary symptoms of OCD, and can also be symptoms of other neurological disorders, including autism spectrum disorder (ASD), depression, psychoneurosis, schizophrenia, and Soto's Syndrome.

The DSM-V defines obsessions as (1) recurrent and persistent thoughts, urges, or impulses that are experienced, at some time during the disturbance, as intrusive and unwanted, and that in most individuals cause marked anxiety or distress; and (2) the individual attempts to ignore or suppress such thoughts, urges, or images, or to neutralize them with some other thought or action (i.e., by performing a compulsion). The DSM-V defines compulsions as (1) repetitive behaviors (e.g., hand washing, ordering, checking) or mental acts (e.g., praying, counting, repeating words silently) that the individual feels driven to perform in response to an obsession or according to rules that must be applied rigidly; and (2) the behaviors or mental acts are aimed at preventing or reducing anxiety or distress, or preventing some dreaded event or situation; however, these behaviors or mental acts are not connected in a realistic way with what they are designed to neutralize or prevent, or are clearly excessive. See DSM-V.

SAD is an anxiety disorder characterized by fear or anxiety specific to social settings, in which a person feels noticed, observed, or scrutinized, and in which the social interactions consistently provoke distress, and in which social interactions are either avoided, or painfully and reluctantly endured. SAD, as used herein, is diagnosed according to the criteria set forth in either of DSM-IV or DSM-V.

Common treatments for the anxiety-related disorders OCD and SAD include cognitive behavior therapy and psychopharmacologic medication. Medications used to treat anxiety-related disorders include serotonin reuptake inhibitors (e.g., Anafranil), selective serotonin reuptake inhibitors (SSRIs; e.g., Sertraline (brand name Zoloft), Fluoxetine (brand name Prozac), Fluvoxamine (brand name Luvox), and Paroxetine (brand name Paxil), Citalopram (brand name Celexa), and Escitalopram (brand name Lexapro)), serotonin-norepinephrine reuptake inhibitors (SNRIs; e.g., Venlafaxine (brand name Effexor), Duloxetine (brand name Cymbalta)).

ASD is currently treated primarily with behavioral therapy such as social skills training, applied behavioral analysis, physical therapy, and occupational therapy. Psychopharmacologic medications, including serotonin reuptake inhibitors (SSRIs), anti-anxiety medications, and stimulants, have been used to treat various symptoms of ASD. For example, risperidone and aripiprazole have been approved to treat irritability associated with autism. Some studies have also shown risperidone, fluvoxamine, fluoxetine, and valproate to help with repetitive behaviors of autism. E. Anagnostou, and E. Hollander, "4 drugs can improve autism's repetitive behaviors" Current Psychiatry. 2006 April; 5(4):55-64.

Psychopharmacologic medications, however, have serious adverse side-effects, including causing suicidal ideation. Thus, a need exists for additional drugs that reduce anxiety in patients with anxiety-related disorders.

SUMMARY

The present invention provides a method of treating an anxiety-related disorder by administering to a subject in need thereof an effective amount of a tyrosine hydroxylase inhibitor. In some embodiments, the anxiety-related disorder is obsessive-compulsive disorder, or social anxiety disorder.

The present invention also provides a method of reducing anxiety, obsessive behavior, or compulsive behavior, by administering to a subject in need thereof an effective amount of a tyrosine hydroxylase inhibitor.

In some embodiments, the tyrosine hydroxylase inhibitor is α-methyl-DL-tyrosine.

In other embodiments, the invention provides pharmaceutical compositions comprising a tyrosine hydroxylase inhibitor. Also provided are kits comprising a tyrosine hydroxylase inhibitor together with packaging for same.

DETAILED DESCRIPTION OF ILLUSTRATIVE EMBODIMENTS

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment incudes from the one particular and/or to the other particular value. Similarly, when values are expressed as approximations, by use of the antecedent "about," it is understood that the particular value forms another embodiment. All ranges are inclusive and combinable.

As used herein, the terms "component," "composition," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

As used herein, the terms "treatment" or "therapy" (as well as different forms thereof) include preventative (e.g., prophylactic), curative or palliative treatment. As used herein, the term "treating" includes alleviating or reducing at least one adverse or negative effect or symptom of a condition, disease or disorder.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

Within the present invention, the disclosed compounds may be prepared in the form of pharmaceutically acceptable salts. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol or neutralizing a free carboxylic acid with an alkali metal base such as a hydroxide, or with an amine.

Compounds described herein can be prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein that contain, for example, both amino and carboxy groups, also include reference to their corresponding zwitterions.

The term "stereoisomers" refers to compounds that have identical chemical constitution but differ as regards the arrangement of the atoms or groups in space. The term "enantiomers" refers to stereoisomers that are mirror images of each other that are non-superimposable.

The term "administering" means either directly administering a compound or composition of the present invention, or administering a prodrug, derivative or analog which will form an equivalent amount of the active compound or substance within the body.

The terms "subject," "individual," and "patient" are used interchangeably herein, and refer to a human, to whom treatment, including prophylactic treatment, with the pharmaceutical composition according to the present invention, is provided.

The term "inhibitor" as used herein includes compounds that inhibit the expression or activity of a protein, polypeptide or enzyme and does not necessarily mean complete inhibition of expression and/or activity. Rather, the inhibition includes inhibition of the expression and/or activity of a protein, polypeptide or enzyme to an extent, and for a time, sufficient to produce the desired effect.

The present invention provides a method of treating an anxiety-related disorder by administering to a subject in need thereof an effective amount of a tyrosine hydroxylase inhibitor.

As used herein, the term "anxiety-related disorder" refers to obsessive-compulsive disorder (OCD), Generalized Anxiety Disorder (GAD), Panic Disorder, Post-traumatic Stress Disorder (PTSD), and social anxiety disorder (SAD).

In some embodiments, the anxiety-related disorder is OCD. As used herein, OCD refers to the condition as diagnosed according to the DSM-IV or DSM-V criteria.

In some embodiments, the anxiety-related disorder is SAD. As used herein, SAD refers to the condition as diagnosed according to the DSM-IV or DSM-V criteria.

In some embodiments, the anxiety-related disorder is OCD or SAD.

In some embodiments, the anxiety-related disorder is GAD. As used herein, GAD refers to the condition as diagnosed according to the DSM-IV or DSM-V criteria.

In some embodiments, the anxiety-related disorder is Panic Disorder. As used herein, Panic Disorder refers to the condition as diagnosed according to the DSM-IV or DSM-V criteria.

In some embodiments, the anxiety-related disorder is PTSD. As used herein, PTSD refers to the condition as diagnosed according to the DSM-IV or DSM-V criteria.

In some aspects the present invention is directed to methods of reducing anxiety, obsessive behavior, or compulsive behavior, by administering to a subject in need thereof an effective amount of a tyrosine hydroxylase inhibitor.

In some embodiments, the methods of the invention are directed to reducing anxiety. As used herein, anxiety may include: fear associated with meeting and talking to people, avoidance of social situations that would elicit significant anxiety in the past, anxiety in anticipation of a social situation, or an inability to initiate conversation with others.

In such embodiments, the methods are performed on a subject who experiences anxiety. Anxiety is a symptom of a number of conditions, including PTSD, ASD, OCD, GAD, and SAD. In some embodiments, the subject who experiences anxiety has been diagnosed with ASD. As used herein, ASD encompasses ASD as diagnosed according to the guidelines set forth in the DSM-V and also the diagnoses of "Autistic Disorder," "Pervasive Developmental Disorder," "Asperger's Disorder," "Rhett's Disorder," or "Childhood Disintegrative Disorder" as rendered under the previous version of the DSM (i.e., DSM-IV).

In other embodiments, the subject who experiences anxiety has been diagnosed with OCD. In some embodiments, the subject who experiences anxiety has been diagnosed with GAD. In some embodiments, the subject who experiences anxiety has been diagnosed with SAD. In some embodiments, the subject who experiences anxiety has been diagnosed with ASD.

In other embodiments, the present invention is directed to methods of reducing obsessive or compulsive behaviors in a subject in need thereof, said method comprising administering to a subject in need thereof an effective amount of a tyrosine hydroxylase inhibitor.

In some embodiments, obsessive or compulsive behaviors include ritualistic and repetitive/restricted behaviors, and obsessive thinking make it difficult for the patient to complete a task or concentrate in a conversation.

In such embodiments, the methods are performed on a subject who experiences obsessions or compulsions. Obsessions or compulsions are symptoms of a number of conditions, including obsessive-compulsive disorder (OCD), autism spectrum disorder (ASD), depression, psychoneurosis, schizophrenia, and Soto's Syndrome. In some embodiments, the subject who experiences obsessions or compulsions has been diagnosed with OCD. In other embodiments, the subject who experiences obsessions or compulsions has been diagnosed with ASD. In some embodiments, the subject who experiences obsessions or compulsions has been diagnosed with depression. In other embodiments, the subject who experiences obsessions or compulsions has been diagnosed with psychoneurosis. In some embodiments, the subject who experiences obsessions or compulsions has been diagnosed with schizophrenia. In other embodiments, the subject who experiences obsessions or compulsions has been diagnosed with a recognized anxiety-related syndrome such as Soto's Syndrome. In some embodiments, the methods of the present disclosure are performed on a subject that is diagnosed with both ASD and another form of anxiety, e.g. OCD.

The present invention is aimed at reducing obsessive or compulsive behavior.

As used herein, obsessive behaviors are behaviors that meet the definition of obsessions set forth in DSM-V. Obsessive behavior, or obsessions, as used herein, are defined under DSM-V, by (1) and (2): (1) recurrent and persistent thoughts, urges, or impulses that are experienced, at some time during the disturbance, as intrusive and unwanted, and that in most individuals cause marked anxiety or distress; and (2) the individual attempts to ignore or suppress such thoughts, urges, or images, or to neutralize them with some other thought or action (i.e., by performing a compulsion).

As used herein, compulsive behaviors are behaviors that meet the definition of compulsions set forth in DSM-V. Compulsive behavior, or compulsions, as used herein, are defined under DSM-V by (1) and (2): (1) repetitive behaviors (e.g., hand washing, ordering, checking) or mental acts (e.g., praying, counting, repeating words silently) that the individual feels driven to perform in response to an obsession or according to rules that must be applied rigidly; and (2) the behaviors or mental acts are aimed at preventing or reducing anxiety or distress, or preventing some dreaded event or situation; however, these behaviors or mental acts are not connected in a realistic way with what they are designed to neutralize or prevent, or are clearly excessive. See DSM-V.

In some embodiments, the methods of the present disclosure reduce obsessive behaviors in a patient in need thereof. In other embodiments, the methods of the present disclosure reduce compulsive behaviors in a patient in need thereof. In some embodiments, the methods of the present disclosure reduce obsessive behaviors and compulsive behaviors in a patient in need thereof.

As used herein, the term "reducing" as used in relation to anxiety, or obsessive or compulsive behaviors, refers to a diminishment in the frequency or severity of the symptom in question. A reduction can be detected by measuring the frequency or severity of the symptom at baseline (i.e., the beginning of treatment) and again after a period of treatment. In some embodiments, the period of treatment is 4 weeks.

Assessment of the frequency or severity of anxiety can be performed using any clinically recognized assessment instrument such as, for example, the Generalized Anxiety Disorder 7-item (GAD-7) scale (Source: Spitzer R L, Kroenke K, Williams J B W, Lowe B. A brief measure for assessing generalized anxiety disorder. Arch Intern Med. 2006; 166:1092-1097), the Hamilton Anxiety Rating Scale (HAM-A), Generalized Anxiety Disorder Severity Scale (GADSS), the Beck Anxiety Inventory (BAI), the Trait Anxiety subscale of the State-Trait Anxiety Inventory (STAI-T), and the Penn State Worry Questionnaire (PSWQ), the Liebowitz Social Anxiety Scale, the Social Phobia Inventory, the Brief Social Phobia Scale, the Disability Profile, the Liebowitz Self-Rated Disability Scale, the Social Phobia Safety Behaviors Scale and the Self-Statements During Public Speaking Scale, the Aberrant Behavior Checklist-Community, the Spence Children's Anxiety Scale, the Social Responsiveness Scale, and the Clinical Global Impression Scale. See World J Psychiatry. 2012 Oct. 22; 2(5): 83-85. See also, Osório F L, Crippa J A S, Loureiro S R. Instruments for the Evaluation of Social Phobia. In: Axelby C P, editor. Social Phobia: Etiology, Diagnoses and Treatment. Hauppauge: Nova Science Publishers; 2009. pp. 1-66.

Assessment of the frequency or severity of obsessive and compulsive behaviors can be performed using any clinically recognized assessment instrument such as, for example, the Yale-Brown Obsessive-Compulsive Scale (YBOCS), the Children's Yale-Brown Obsessive-Compulsive Scale (CY-BOCS), and/or self-reporting instruments such as the Obsessive-Compulsive Inventory (OCI; OCI-R), the Padua Inventory, the Repetitive Behavior Scale, the Spence Children's' Anxiety Scale, the Social Responsiveness Scale, the Clinical Global Impression Scale.

The methods of the present disclosure comprise administering to a subject in need thereof an effective amount of a tyrosine hydroxylase inhibitor or a pharmaceutically acceptable salt thereof. As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with respect to the particular compound, component or composition selected, concomitant medications, the route of administration, and the ability of the components to elicit a desired result in the individual, but also with respect to factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage being at the discretion of the attending physician. Dosage regimes may be adjusted to provide improved therapeutic response. An effective amount is also one in which any toxic or detrimental effects of the components are outweighed by the therapeutically beneficial effects.

Administration of the tyrosine hydroxylase inhibitor according to the methods of the present disclosure can be through various routes, including orally, nasally subcutaneously, intravenously, intramuscularly, transdermally, vaginally, rectally or in any combination thereof.

In certain embodiments, the tyrosine hydroxylase inhibitor is a tyrosine derivative. The tyrosine derivative can be capable of existing in different isomeric forms, including stereoisomers and enantiomers. The tyrosine derivative can, for example, exist in both L-form or D-form. The tyrosine derivative can, for example, also exist in a racemic form. Representative tyrosine derivatives include one or more of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-tyrosine(tBu)-allyl ester hydrochloride, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy] benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyrosine methyl ester hydrochloride, H-3,5-diiodo-tyrosine methyl ester hydrochloride, H-D-3,5-diiodo-tyrosine methyl ester hydrochloride, H-D-tyrosine methyl ester hydrochloride, D-tyrosine methyl ester hydrochloride, D-tyrosine-methyl ester hydrochloride, methyl D-tyrosinate hydrochloride, H-D-tyrosine methyl ester.hydrochloride, D-tyrosine methyl ester hydrochloride, H-D-tyrosine methyl ester-hydrochloride, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-tyrosine (3,5-I2)-OSu, Fmoc-tyrosine(3-NO2)-OH, α-methyl-L-tyrosine, α-methyl-D-tyrosine, α-methyl-DL-tyrosine, and $C_1$-$C_{12}$ alkyl ester salts of α-methyl-DL-tyrosine such as α-methyl-DL-tyrosine methyl ester hydrochloride.

In certain embodiments of the invention, the tyrosine derivative is α-methyl-L-tyrosine. In other embodiments, the tyrosine derivative is α-methyl-D-tyrosine. In other embodiments, the tyrosine derivative is α-methyl-DL-tyrosine in a racemic form.

In one suitable embodiment of the invention, the tyrosine hydroxylase inhibitor is administered daily. In another suitable embodiment of the invention, the tyrosine hydroxylase inhibitor is administered in divided doses. In some embodiments, the tyrosine hydroxylase inhibitor is administered three times per day. In some embodiments the tyrosine hydroxylase inhibitor is required chronically, while in others it may be discontinued after satisfactory results are obtained. In some embodiments, the tyrosine hydroxylase inhibitor has a plasma half life ($t_{1/2}$) of 6-12 hours. In such embodiments, the tyrosine hydroxylase inhibitor is preferably administered two- to three-times daily.

In some aspects, about 10-2000 mg of the tyrosine hydroxylase inhibitor (e.g., α-methyl-DL-tyrosine) is administered daily, preferably, 100-1200 mg of the tyrosine hydroxylase inhibitor is administered daily, most preferably, 200-900 mg of the tyrosine hydroxylase inhibitor (e.g., α-methyl-DL-tyrosine) is administered daily. The tyrosine hydroxylase inhibitor (e.g., α-methyl-DL-tyrosine) is preferably administered orally. The daily dosages can be administered as a single dose or as divided doses throughout the day. Divided dosing is particularly preferred. The daily dosages can be administered as divided, substantially equal doses.

Preferred aspects of the disclosure are directed to methods of reducing obsessions or compulsions in a patient by administering an effective amount of α-methyl-DL-tyrosine to the patient. These methods result in the reduction of at least one of the patient's obsessive or compulsive behaviors as defined in the DSM-5. In some embodiments, these methods also result in a reduction of at least one of the dimensions of obsessive or compulsive behavior assessed using the Aberrant Behavior Checklist-Community (ABC-C), Autism Diagnostic Observation Schedule (ADOS), Conners Parent Rating Scale (CPRS), Yale-Brown Obsessive-Compulsive Scale (YBOCS), the Children's Yale-Brown Obsessive-Compulsive Scale (CYBOCS), the Obsessive-Compulsive Inventory (OCI; OCI-R), the Padua Inventory, the Repetitive Behavior Scale, the Spence Children's' Anxiety Scale, the Social Responsiveness Scale, or the Clinical Global Impression Scale. According to these aspects, about 10-2000 mg of the α-methyl-DL-tyrosine is administered daily, preferably, 100-1200 mg of the α-methyl-DL-tyrosine is administered daily, and more preferably 200-900 mg of the α-methyl-DL-tyrosine is administered daily. The α-methyl-DL-tyrosine is preferably administered orally. The daily dosages can be administered as a single dose or in divided doses throughout the day. The daily dosages can be administered as divided, substantially equal doses. Three, substantially equal daily doses of the α-methyl-DL-tyrosine are particularly preferred.

In some embodiments of the invention, methods further comprising assessing the obsessive or compulsive behaviors in the subject are provided. This assessing step can be performed before said administering step or after said administering step. The assessing step may be performed using an assessment instrument appropriate to the behavior of interest, and may include one or more of the standard assessment tools known in the art, including for example, the Vineland Adaptive Behavior Scale $2^{nd}$ edition (VABS II, VABS) questionnaire, the Autism Diagnostic Observation Schedule (ADOS), the Aberrant Behavior Checklist-Community (ABC-C), the Spencer Anxiety Scale (SAS), the Repetitive Behavior Score-Revised (RBS-R), the Social Responsiveness Scale (SRS), the Conners Parent Rating Scale, the Yale-Brown Obsessive-Compulsive Scale (YBOCS), the Children's Yale-Brown Obsessive-Compulsive Scale (CYBOCS), the Obsessive-Compulsive Inventory (OCI; OCI-R), the Padua Inventory, the Repetitive Behavior Scale, the Spence Children's' Anxiety Scale, the Social Responsiveness Scale, or the Clinical Global Impression Scale. The assessing step may also be performed by clinical observation by the physician who is treating the patient.

Other preferred aspects of the disclosure are directed to methods of reducing anxiety in a patient by administering an effective amount of α-methyl-DL-tyrosine to the patient. These methods result in the reduction of the patient's anxiety. In some embodiments, these methods result in a reduction of at least one of the dimensions of anxiety assessed using one of the Hamilton Anxiety Rating Scale (HAM-A), Generalized Anxiety Disorder Severity Scale (GADSS), the Beck Anxiety Inventory (BAI), the Trait Anxiety subscale of the State-Trait Anxiety Inventory (STAI-T), and the Penn State Worry Questionnaire (PSWQ), the Liebowitz Social Anxiety Scale, the Social Phobia Inventory, the Brief Social Phobia Scale, the Disability Profile, the Liebowitz Self-Rated Disability Scale, the Social Phobia Safety Behaviors Scale and the Self-Statements During Public Speaking Scale, Social Phobic Disorders Severity and Change Form (SPD-SC Form), the Aberrant Behavior Checklist-Community, the Spence Children's Anxiety Scale, the Social Responsiveness Scale, and the Clinical Global Impression Scale. According to these aspects, about 10-2000 mg of the α-methyl-DL-tyrosine is administered daily, preferably, 100-1200 mg of the α-methyl-DL-tyrosine is administered daily, and more preferably 200-900 mg of the α-methyl-DL-tyrosine is administered daily. The α-methyl-DL-tyrosine is preferably administered orally. The daily dosages can be administered as a single dose or in divided doses throughout the day. The daily dosages can be administered as divided, substantially equal doses. Three, substantially equal daily doses of the α-methyl-DL-tyrosine are particularly preferred.

In some embodiments of the invention, methods further comprising assessing the anxiety in the subject are provided. This assessing step can be performed before said administering step or after said administering step. The assessing step may be performed using an assessment instrument appropriate anxiety symptoms, and may include one or more of the standard assessment tools known in the art, including for example, the Vineland Adaptive Behavior Scale $2^{nd}$ edition (VABS II, VABS) questionnaire, the Autism Diagnostic Observation Schedule (ADOS), the Aberrant Behavior Checklist-Community (ABC-C), the Spencer Anxiety Scale (SAS), the Repetitive Behavior Score-Revised (RBS-R), the Social Responsiveness Scale (SRS), the Conners Parent Rating Scale, the Yale-Brown Obsessive-Compulsive Scale (YBOCS), the Children's Yale-Brown Obsessive-Compulsive Scale (CYBOCS), the Obsessive-Compulsive Inventory (OCI; OCI-R), the Padua Inventory, Hamilton Anxiety Scale (HAM-A), the Liebowitz Social Anxiety Scale (LSAS) the Social Phobic Disorders Severity and Change Form (SPD-SC Form), the Generalized Anxiety Disorder Severity Scale (GADSS), the Beck Anxiety Inventory (BAI), the Trait Anxiety subscale of the State-Trait Anxiety Inventory (STAI-T), the Penn State Worry Questionnaire (PSWQ), the Brief Social Phobia Scale, the Disability Profile, the Liebowitz Self-Rated Disability Scale, the Social Phobia Safety Behaviors Scale or the Self-Statements During Public Speaking Scale, Aberrant Behavior Checklist-Community, the Spence Children's Anxiety Scale, the Social Responsiveness Scale, and/or the Clinical Global Impression Scale. The assessing step may also be performed by clinical observation by the physician who is treating the patient.

In some embodiments of the present methods, the tyrosine hydroxylase inhibitor is administered to the patient in combination with other medications. As used herein, administering drugs in combination does not imply any particular dosing regimen, but rather means that both drugs are present in or on the patient's body at the same time. Thus, drugs administered in combination may be administered simultaneously, or may be administered sequentially (e.g., at different times during the day).

In some embodiments, the tyrosine hydroxylase inhibitor is administered in combination with γ-aminobutyric acid (GABA). The GABA can be administered simultaneously with the tyrosine hydroxylase inhibitor. In other aspects, the GABA can be administered separately from the tyrosine hydroxylase inhibitor, i.e., at another time during the day. In some aspects the GABA is administered at bedtime. Typically, dosages of the GABA are from about 5 mg to about 30 mg, for example, 5, 10, 15, 20, 25, or about 30 mg of GABA, with 15 mg of GABA being particularly preferred.

Thus, in some embodiments, the present disclosure provides methods of treating anxiety-related disorders, or methods of reducing anxiety, obsessive behavior, or compulsive behaviors in a subject in need thereof, comprising administering to a subject in need thereof an effective amount of a tyrosine hydroxylase inhibitor and GABA. In some embodiments, the disclosure provides methods of treating anxiety-related disorders, or methods of reducing anxiety, obsessive behaviors, or compulsive behaviors in a subject in need thereof, comprising administering to a subject in need thereof an effective amount of α-methyl-DL-tyrosine and GABA.

In other embodiments, the tyrosine hydroxylase inhibitor is administered in combination with serotonin or melatonin, or pharmaceutically acceptable salts thereof. The serotonin or melatonin can be administered simultaneously with the tyrosine hydroxylase inhibitor. In other aspects, the serotonin or melatonin can be administered separately from the tyrosine hydroxylase inhibitor, i.e., at another time during the day. In some aspects the serotonin or melatonin is administered at bedtime. In some embodiments, the present disclosure provides methods of treating anxiety-related disorders, or methods of reducing anxiety, obsessive behavior, or compulsive behaviors in a subject in need thereof, comprising administering to a subject in need thereof an effective amount of a tyrosine hydroxylase inhibitor and serotonin or melatonin. In some embodiments, the disclosure provides methods of treating anxiety-related disorders, or methods of reducing anxiety, obsessive behaviors, or compulsive behaviors in a subject in need thereof, comprising administering to a subject in need thereof an effective amount of α-methyl-DL-tyrosine and serotonin or melatonin, or pharmaceutically acceptable salts thereof.

In other aspects, the tyrosine hydroxylase inhibitor is administered in combination with another drug commonly used in treating ASD, attention deficit hyperactivity disorder (ADHD), OCD, GAD, or SAD. For example, the tyrosine hydroxylase inhibitor can be administered together with drugs that affect neurotransmission (e.g. amphetamine, methylphenidate, and the like), such as psychotropic drugs (e.g., risperidone), neurotransmitter reuptake inhibitors (e.g., fluoxetine), compounds that stimulate glutaminergic transmission (e.g., LY2140023), and/or compounds that affect cholinergic, serotonergic, vasopressin, oxytocin, or glutamate modulated neurotransmission (e.g., galantamine), or pharmaceutically acceptable salts thereof. As such, the disclosure is also directed to methods wherein an effective amount of a tyrosine hydroxylase inhibitor (e.g., α-methyl-DL-tyrosine) is administered in combination with an effective amount of a compound that affects neurotransmission, such as a psychotropic drug, a neurotransmitter reuptake inhibitor, a compound that stimulates glutaminergic transmission, and/or a compound that affects cholinergic, serotonergic, vasopressin, oxytocin, or glutamate modulated neurotransmission, or pharmaceutically acceptable salts thereof.

In some embodiments, the tyrosine hydroxylase inhibitor is administered in combination with a beta-adrenergic agonist (also referred to as beta agonists) such as, for example, albuterol, levalbuterol, fenoterol, formoterol, isoproterenol, metaproterenol, salmeterol, terbutaline, clenbuterol, isoetarine, pirbuterol, procaterol, ritodrine, epinephrine, or pharmaceutically acceptable salts thereof, and combinations thereof. Albuterol is a particularly preferred beta-adrenergic agonist.

In other embodiments, the tyrosine hydroxylase inhibitor is administered in combination with psychopharmacologic drugs such as, for example, aripiprazole, pimavanserin, olanzapine, asenapine, clozapine, quetiapine, risperidone, lurasidone, cariprazine, paliperidone, brexpiprazole, iloperidone, ziprasidone, or balovaptan, or pharmaceutically acceptable salts thereof. In preferred embodiments, the tyrosine hydroxylase inhibitor is α-methyl-DL-tyrosine and the psychopharmacologic drug is aripiprazole, risperidone, or balovaptan.

In other embodiments, the tyrosine hydroxylase inhibitor is administered in combination with vasopressin or vasopressin analogs, such as, for example, desmopressin, felypressin, ornipressin, selepressin, and terlipressin. In some embodiments, the tyrosine hydroxylase inhibitor is administered in combination with desmopressin.

In other embodiments, the tyrosine hydroxylase inhibitor is administered in combination with an antidepressant drug such as, for example, selective serotonin reuptake inhibitors (SSRIs) (e.g., fluoxetine, sertraline, citalopram, escitalopram, fluvoxamine, and paroxetine, or pharmaceutically acceptable salts thereof). In preferred embodiments, the tyrosine hydroxylase inhibitor is α-methyl-DL-tyrosine and the antidepressant drug is fluoxetine or sertraline.

In other embodiments, the tyrosine hydroxylase inhibitor is administered in combination with other anti-anxiety drugs, for example, barbiturates, carbamates, antihistamines (e.g., hydroxyzine, chlorpheniramine, or diphenhydramine), opioids (e.g., hydrocodone, fentanyl, buprenorphine), benzodiazepines (e.g., alprazolam, clonazepam, diazepam, lorazepam, oxazepam, chlordiazepoxide), beta blockers (e.g., propranolol, atenolol), tricyclic antidepressants (e.g., imipramine, desipramine, nortriptyline, amitriptyline, doxepin, clomipramine), tetracyclic antidepressants (e.g., mirtazapine), other antidepressants, (e.g., trazodone), monoamine oxidase inhibitors (MAOIs) (e.g., phenelzine, tranylcypromine, isocarboxazid, moclobemide), serotonin-norepinephrine reuptake inhibitors (SNRIs) (e.g., venlafaxine, duloxetine), mild tranquilizers (e.g., buspirone), anticonvulsants (valproate, pregabalin, gabapentin), bupropion, alpha blockers (e.g., prazosin), or pharmaceutically acceptable salts thereof.

While not intending to be bound by any particular mechanism of operation, it is believed that the tyrosine hydroxylase inhibitors according to the present invention function by inhibiting the first, and rate limiting, step in catecholamine synthesis, i.e., the conversion of tyrosine to dihydroxyphenylalanine (DOPA), and thus reduce the synthesis and subsequent synaptic release of dopamine (DA), norepinephrine (NE), and epinephrine (E).

Also provided herein are kits comprising a tyrosine hydroxylase inhibitor together with packaging for same. In some embodiments, the kits further comprise other drugs useful in treating OCD, or SAD, including, for example, GABA, serotonin, melatonin, beta adrenergic agonist, anti-anxiety drugs, psychopharmacologic drugs, antidepressants. In some embodiments, the kits comprise a tyrosine hydroxylase inhibitor, and a drug selected from albuterol, alprazolam, amitriptyline, aripiprazole, asenapine, atenolol, balovaptan, brexpiprazole, buprenorphine, bupropion, buspirone, cariprazine, chlordiazepoxide, chlorpheniramine, citalopram, clenbuterol, clomipramine, clonazepam, clozapine, desipramine, diazepam, diphenhydramine, doxepin, duloxetine, epinephrine, escitalopram, fenoterol, fentanyl, fluoxetine, fluvoxamine, formoterol, gabapentin, hydrocodone, hydroxyzine, iloperidone, imipramine, isocarboxazid, isoetarine, isoproterenol, levalbuterol, lorazepam, lurasidone, metaproterenol, mirtazapine, moclobemide, nortriptyline, olanzapine, oxazepam, paliperidone, paroxetine, phenelzine, pimavanserin, pirbuterol, prazosin, pregabalin, procaterol, propranolol, quetiapine, risperidone, ritodrine, salmeterol, sertraline, terbutaline, tranylcypromine, trazodone, valproate, venlafaxine, desmopressin, felypressin, ornipressin, selepressin, terlipressin. or ziprasidone, or pharmaceutically acceptable salts thereof. Such kits are useful in performing the methods of the present disclosure. The tyrosine hydroxylase inhibitor can be a tyrosine derivative. The tyrosine derivative can include tyrosine derivatives capable of existing in isomeric form. The tyrosine derivatives can include tyrosine derivatives in its L-form or in its D-form. The tyrosine derivative can, for example, also exist in a racemic form. Representative tyrosine derivatives include one or more of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-tyrosine(tBu)-allyl ester hydrochloride, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy] benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyrosine-methyl ester hydrochloride, H-3,5-diiodo-tyrosine-methyl ester hydrochloride, H-D-3,5-diiodo-tyrosine-methyl ester hydrochloride, H-D-tyrosine-methyl ester hydrochloride, D-tyrosine methyl ester hydrochloride, D-tyrosine-ome hydrochloride, methyl D-tyrosinate hydrochloride, H-D-tyrosine-methyl ester.hydrochloride, D-tyrosine methyl ester hydrochloride, H-D-tyrosine-methyl ester-hydrochloride, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-tyrosine (3,5-I2)-OSu, Fmoc-tyrosine(3-NO2)-OH, α-methyl-L-tyrosine, α-methyl-D-tyrosine, and α-methyl-DL-tyrosine. In certain embodiments of the invention, the tyrosine derivative is α-methyl-L-tyrosine. In other specific embodiments of the invention, the tyrosine derivative is α-methyl-D-tyrosine. In other embodiments, the tyrosine derivative is α-methyl-DL-tyrosine in a racemic form.

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

Example 1

In the course of the study described below, patients with OCD or SAD were observed to have improved anxiety-related symptoms.

Study Title: A Double Blinded, Randomized, Placebo Controlled, Dose Ranging Study for the use of L1-79 in the Treatment of Autism Study Design: Blinded, randomized, 4-arm, 4-week treatment period. Treatment arms consist of α-methyl-DL-tyrosine (i.e., L1-79) in doses of 100 mg, or 200 mg, or placebo tid.

Sample Size:N=30; randomized and 10 open label to 4 groups:

| Group 1 (n = 10) | 100 mg L1-79 (1 × 100 mg capsule + 1 placebo) TID |
| Group 2 (n = 5) | 100 mg L1-79 (1 × 100 mg capsule + 1 placebo) TID |
| Group 3 (n = 10) | 200 mg L1-79 (2 × 100 mg capsules) TID |
| Group 4 (n-5) | 200 mg L1-79 (2 × 100 mg capsules) TID |
| Group 5 (n = 10) | Placebo (3 placebo) TID |

Study Population: Male subjects between the ages of 13 and 21 years of age, diagnosed with autism who that meet the entry criteria and who are able to complete standardized measures allowing them to participate in this study.

Major Inclusion Criteria: Males between 13 and 21 years of age, signed informed consent, normal clinical laboratory values, DSM-5 compliant diagnosis of autism spectrum disorder, confirmed by the Autistic Diagnosis Interview Review (ADIR), and by the Autism Diagnosis Observation Schedule (ADOS) score consistent with a diagnosis of autism. No more than one concomitant medication, stable concomitant medications for at least 2 weeks prior to enrollment and no planned changes in psychosocial interventions during the trial.

Major Exclusion Criteria: Any co-morbidities, including Fragile-X syndrome, epilepsy, Retts syndrome, ADHD, or other disease or syndrome aside from autism that requires treatment. Any other psychiatric disorder, or out of range lab values. DSM-5 diagnosis of schizophrenia, schizoaffective disorder, alcohol use disorder; active medical problems: unstable seizures (>2 in past month), significant physical illness;

Experimental Treatment: L1-79 at doses of 100 or 200 mg three times daily for 4 weeks.

Non-Experimental Treatment: Placebo.

Dosage and Administration: L1-79 or placebo, as randomized, were administered orally according to the regimen above.

Evaluation Schedule: Subjects were evaluated within one week prior to study accession, and weekly throughout the dosing period, and again 4 weeks after the cessation of treatment.

Safety Measures: Regularly scheduled complete history and physical examination that included orthostatic blood pressure measurements, vital signs, CBC, differential, platelet counts, urine analysis, serum enzymes including: total protein, albumin, glucose, BUN, creatinine, direct and total bilirubin, alkaline phosphatase, phosphorous, calcium, AST, ALT, sodium, potassium, chloride, bicarbonate, $T_4$, TSH, and adverse events assessments. Electrocardiograms were taken at the study screening visit and at the week 4 treatment visit (end of dosing).

Study Endpoints: The primary end point was an assessment of the safety of L1-79 based upon reported adverse events and changes in baseline in physical examination parameters that included orthostatic blood pressure, clinical laboratory measures, and ECGs. Secondary endpoints will include the attending physicians assessment as quantified by the Clinical Global Impressions scale based upon changes from baseline in various psychometric tests, including the Vineland Adaptive Behavior Scale $2^{nd}$ edition (VABS II, VABS) questionnaire, the Autism Diagnostic Observation Schedule (ADOS), the Aberrant Behavior Checklist-Community (ABC-C), the Spencer Anxiety Scale (SAS), the Repetitive Behavior Score-Revised (RBS-R), the Social Responsiveness Scale (SRS), as well as from their personal observations in the clinic, and from videographic information taken during ADOS testing (per this protocol) and anecdotally as provided by caregivers over the course of this study.

Improvement in Obsessive-Compulsive Symptoms

In the course of this study, patients diagnosed with Autistic Spectrum Disorder and one or more of Obsessive Compulsive Disorder and Attention Deficit/Hyperactivity Disorder experienced reductions in obsessive-compulsive symptoms, as shown by the case studies below.

Obsessive-compulsive symptoms can include ritualistic and repetitive/restricted behaviors, and obsessive thinking make it difficult for the patient to complete a task or concentrate in a conversation.

All of the patients were receiving L1-79 100-200 mg three times a day. None of the patients in the OCD symptom improvement group were receiving medication for Obsessive Compulsive Disorder Obsessive-compulsive symptoms were initially recorded at baseline, and at end of active treatment using the Repetitive Behavior Scale, the Spence Children's' Anxiety Scale, the Social Responsiveness Scale, the Clinical Global Impression Scale and direct parent report.

Subject 02-002 showed a decrease in OCD symptoms as measured by a decrease from a Severe score of 96 to a Moderate score of 73 on SRS/DSM-5 in Repetitive Behavior and Restrictive Interests.

Subject 02-003 showed improvement in OCD symptoms at week 4 going from Severe to Moderate on the SRS/DSM-5 in Repetitive Behavior and Restrictive Interests.

Subject 02-004 was scored "Much Improved" on the Stereotypic and Restricted Interests section of the CGI-I.

Subject 02-007 OCD symptoms decreased from Moderate to Within Normal Limits on the SRS/DSM-5 subscale of Repetitive Behaviors and Restricted Interests; as well as on the Spence Children's Anxiety Scale OCD score (3.0 for anxiety disordered children to 0 for normal/no OCD)

Subject 02-012 showed normalization in OCD symptoms on the SRS/DSM-5 Repetitive Behavior and Restrictive Interests going from a score of 80 (Severe) to a score of 46 (Within Normal Limits) and a score of "Much Improved" on the CGI-I. Parent commented, "His fixations aren't as present."

Subject 02-16 went from SRS/DSM-5 Repetitive Behavior and Restrictive Interests going from a score of 65 (Mild) to a score of 46 (Within Normal Limits). The CGI-Severity scale went from Mildly Ill in the area of Stereotyped Behaviors and Restricted Interests to Normal.

Subject 02-020 showed improvement in OCD symptoms on the SRS/DSM-5 Repetitive Behavior and Restrictive Interests going from a score of 85 (Severe) to a score of 73 (Moderate).

One patient who could not talk about anything other than his area of obsessive interest at baseline was, after 4 weeks on active drug, able to have conversations about things of interest to others, as he was less preoccupied with his own obsessive thoughts.

One patient who experienced self-injurious compulsive behaviors at baseline had, after 3 weeks on active drug, completely stopped self-injury.

Improvement in Social Anxiety Symptoms

In the course of this study, patients diagnosed with Autistic Spectrum Disorder and one or more of Social Anxiety Disorder and Generalized Anxiety Disorder, experienced reductions in social-anxiety symptoms as shown by the case studies below.

Social anxiety symptoms included one or more of fear associated with meeting and talking to people, avoidance of social situations that would elicit significant anxiety in the past, anxiety in anticipation of a social situation, and an inability to initiate conversation with others. The presence of the social anxiety symptoms was recorded at baseline using the Aberrant Behavior Checklist-Community, the Spence Children's Anxiety Scale, the Social Responsiveness Scale, and/or the Clinical Global Impression Scale and direct parent report.

All of the patients were receiving L1-79 100-200 mg three times a day. None of the patients in the Social Anxiety symptom improvement group were receiving medication for Social Anxiety Disorder Subject 02-002 showed a significant improvement on the ABC-C in the area of Social Withdrawal going from the 98% to the 75%. On the SRS/DSM-5 Social Communication scale he went from being in the Severe range to the Moderate range after 4 weeks on L1-79. On the CGI-I in the areas of Social Interaction and Communication at week 4 he was rated at "Much Improved."

Subject 02-007 showed significant improvement on the ABC-C in the area of Social Withdrawal going from the 75% to below the 40% by week 4 of treatment.

Subject 02-009 showed significant improvement on the ABC-C in the area of Social Withdrawal going from the 91% down to the 63% at week 4 of treatment with L1-79.

Subject 02-012 showed significant improvement on the ABC-C in the area of Social Withdrawal going from the 84% to below the 40%. On the SRS/DSM-5 Social Communication scale he went from being in the Severe range to the Within Normal Limits range after 4 weeks on L1-79. On the CGI-I in the areas of Social Interaction and Communication at week 4 he was rated at "Much Improved." The CGI-Severity Score went from Moderately Ill to Borderline Ill.

Subject 02-014 showed improvement in social anxiety symptoms on the CGI-I scoring "Much Improved" on the Social Interactions and Communication area. The CGI-Severity score went from Markedly Ill to Moderately Ill in the Social Interaction area.

Subject 02-016 showed improvement in social anxiety on the SRS/DSM-5 Social Communication scale. He went from being in the Mildly Deficient range to the Within Normal Limits range after 4 weeks on L1-79. On the CGI-I in the areas of Social Interaction and Communication at week 4 he was rated at "Much Improved." The CGI-Severity Score went from Mildly Ill to Normal in the areas of Social Interaction and Communication. At week 4 subject 02-016 stated "I find it easier to talk to other people. I've also noticed that I've been a lot calmer."

Subject 02-022 showed improvement in social anxiety on the CGI-I in the areas of Social Interaction and Communication. At week 4 of treatment with L1-79 he was rated at "Much Improved."

Example 2 Case Study Demonstrating Reduction of Obsessions and Compulsions

An ASD patient (SUBJECT JW) has a history of obsessive thoughts and compulsive behaviors that negatively impact his functioning. The obsessive thoughts make it difficult for JW to engage in meaningful conversations with others or be aware of things around him due to the intensity of the obsessive thoughts. When taking L1-79 (100-200 mg three times per day) there was a significant decrease in obsessive thoughts to the degree that JW was able to engage in meaningful conversation with others, understand concepts and make observations that were otherwise not occurring due to the intensity of the obsessive thoughts. There was also a decrease in rigid and inflexible thinking. Compulsive behaviors/routines could be delayed or skipped, as there were other things of interest that took the place of the need to perform the compulsions or be entrenched in obsessive thinking.

The disclosure is also directed to the following aspects:

Aspect 1. A method of treating an anxiety-related disorder, said method comprising administering to a subject in need thereof an effective amount of a tyrosine hydroxylase inhibitor.

Aspect 2. The method of aspect 1, wherein the anxiety-related disorder is obsessive-compulsive disorder or social anxiety disorder.

Aspect 3. The method of aspect 2, wherein said anxiety-related disorder is obsessive-compulsive disorder.

Aspect 4. The method of aspect 2, wherein said anxiety-related disorder is social anxiety disorder.

Aspect 5. A method of reducing anxiety, obsessive behavior, or compulsive behavior, said method comprising administering to a subject in need thereof an effective amount of a tyrosine hydroxylase inhibitor.

Aspect 6. The method of aspect 5, wherein said method is for reducing anxiety.

Aspect 7. The method of aspect 5, wherein said method is for reducing obsessive behavior or compulsive behavior.

Aspect 8. The method of any one of aspects 1 to 7, wherein said tyrosine hydroxylase inhibitor is methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-tyrosine(tBu)-allyl ester hydrochloride, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy] benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyrosine methyl ester hydrochloride, H-3,5-diiodo-tyrosine methyl ester hydrochloride, H-D-3,5-diiodo-tyrosine methyl ester hydrochloride, H-D-tyrosine methyl ester hydrochloride, D-tyrosine methyl ester hydrochloride, D-tyrosine-methyl ester hydrochloride, methyl D-tyrosinate hydrochloride, H-D-tyrosine methyl ester.hydrochloride, D-tyrosine methyl ester hydrochloride, H-D-tyrosine methyl ester-hydrochloride, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-tyrosine (3,5-I2)-OSu, Fmoc-tyrosine(3-NO2)-OH, α-methyl-L-tyrosine, α-methyl-D-tyrosine, or α-methyl-DL-tyrosine.

Aspect 9. The method of aspect 8 wherein the tyrosine hydroxylase inhibitor is α-methyl-DL-tyrosine.

Aspect 10. The method of anyone of aspects 1 to 9 wherein the tyrosine hydroxylase inhibitor is administered orally.

Aspect 11. The method of any one of the preceding aspects wherein 100-1200 mg of the tyrosine hydroxylase inhibitor is administered daily.

Aspect 12. The method of aspect 11 wherein 200-900 mg of the tyrosine hydroxylase inhibitor is administered daily.

Aspect 13. The method of any one of the preceding aspects wherein the tyrosine hydroxylase inhibitor is administered in divided, substantially equal, doses.

Aspect 14. The method of any one of the preceding aspects further comprising administering an effective amount of GABA.

Aspect 15. The method of any one of the preceding aspects further comprising administering an effective amount of serotonin or melatonin, or a pharmaceutically acceptable salt thereof.

Aspect 16. The method of any one of the preceding aspects further comprising administering an effective amount of vasopressin or a vasopressin analog.

Aspect 17. The method of aspect 16, wherein the vasopressin analog is desmopressin, felypressin, ornipressin, selepressin, or terlipressin.

Aspect 18. The method of any one of the preceding aspects further comprising administering an effective amount of a compound that affects neurotransmission.

Aspect 19. The method of aspect 18, wherein the compound that affects neurotransmission is a psychotropic drug, a neurotransmitter reuptake inhibitor, a compound that stimulates glutaminergic transmission, or a compound that affects cholinergic, serotonergic, vasopressin, oxytocin, or glutamate modulated neurotransmission.

Aspect 20. The method of any one of the preceding aspects further comprising administering an effective amount of a beta-adrenergic agonist, a psychopharmacologic drug, an anti-anxiety drug, or an antidepressant.

Aspect 21. The method of aspect 20 wherein the beta-adrenergic agonist is albuterol, levalbuterol, fenoterol, formoterol, isoproterenol, metaproterenol, salmeterol, terbutaline, clenbuterol, isoetarine, pirbuterol, procaterol, ritodrine, or epinephrine, or a pharmaceutically acceptable salt thereof.

Aspect 22. The method of aspect 20 wherein the psychopharmacologic drug is aripiprazole, pimavanserin, olanzapine, asenapine, clozapine, quetiapine, risperidone, lurasidone, cariprazine, paliperidone, brexpiprazole, iloperidone, ziprasidone, or balovaptan, or a pharmaceutically acceptable salt thereof.

Aspect 23. The method of aspect 20, wherein the anti-anxiety drug is a barbiturate, carbamate, antihistamine, opioids, benzodiazepines, beta blockers, tricyclic antidepressants, tetracyclic antidepressants, monoamine oxidase inhibitors (MAOIs) serotonin-norepinephrine reuptake inhibitors (SNRIs), mild tranquilizers, anticonvulsants, bupropion, or alpha blockers.

Aspect 24. The method of aspect 23, wherein the anti-anxiety drug is hydroxyzine, chlorpheniramine, diphenhydramine, hydrocodone, fentanyl, buprenorphine, alprazolam, clonazepam, diazepam, lorazepam, oxazepam, chlordiazepoxide propranolol, atenolol, imipramine, desipramine, nortriptyline, amitriptyline, doxepin, clomipramine, mirtazapine, trazodone, phenelzine, tranylcypromine, isocarboxazid, moclobemide, escitalopram, citalopram, venlafaxine, duloxetine, buspirone, valproate, pregabalin, gabapentin, bupropion, prazosin, or a pharmaceutically acceptable salt thereof.

Aspect 25. The method of aspect 20 wherein the antidepressant is fluoxetine, sertraline, citalopram, escitalopram, fluvoxamine, or paroxetine, or a pharmaceutically acceptable salt thereof.

Aspect 26. A method of treating an anxiety-related disorder, said method comprising administering to a subject in need thereof an effective amount of a tyrosine hydroxylase inhibitor.

Aspect 27. The method of aspect 26, wherein the anxiety-related disorder is obsessive-compulsive disorder or social anxiety disorder.

Aspect 28. The method of aspect 27, wherein said anxiety-related disorder is obsessive-compulsive disorder.

Aspect 29. The method of aspect 27, wherein said anxiety-related disorder is social anxiety disorder.

Aspect 30. A method of reducing anxiety, obsessive behavior, or compulsive behavior, said method comprising administering to a subject in need thereof an effective amount of a tyrosine hydroxylase inhibitor.

Aspect 31. The method of aspect 30, wherein said method is for reducing anxiety.

Aspect 32. The method of aspect 30, wherein said method is for reducing obsessive behavior or compulsive behavior.

Aspect 33. The method of any one of aspects 26 to 32, wherein said tyrosine hydroxylase inhibitor is methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-tyrosine(tBu)-allyl ester hydrochloride, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy] benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyrosine methyl ester hydrochloride, H-3,5-diiodo-tyrosine methyl ester hydrochloride, H-D-3,5-diiodo-tyrosine methyl ester hydrochloride, H-D-tyrosine methyl ester hydrochloride, D-tyrosine methyl ester hydrochloride, D-tyrosine-methyl ester hydrochloride, methyl D-tyrosinate hydrochloride, H-D-tyrosine methyl ester.hydrochloride, D-tyrosine methyl ester hydrochloride, H-D-tyrosine methyl ester-hydrochloride, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-tyrosine (3,5-I2)-OSu, Fmoc-tyrosine(3-NO2)-OH, α-methyl-L-tyrosine, α-methyl-D-tyrosine, α-methyl-DL-tyrosine, or $C_1$-$C_{12}$ alkyl ester salts of α-methyl-DL-tyrosine such as α-methyl-DL-tyrosine methyl ester hydrochloride.

Aspect 34. The method of aspect 33 wherein the tyrosine hydroxylase inhibitor is α-methyl-DL-tyrosine.

Aspect 35. The method of anyone of aspects 26 to 34 wherein the tyrosine hydroxylase inhibitor is administered orally.

Aspect 36. The method of any one of aspects 26 to 35 wherein 100-1200 mg of the tyrosine hydroxylase inhibitor is administered daily.

Aspect 37. The method of aspect 36 wherein 200-900 mg of the tyrosine hydroxylase inhibitor is administered daily.

Aspect 38. The method of any one of aspects 26 to 37 wherein the tyrosine hydroxylase inhibitor is administered in divided, substantially equal, doses.

Aspect 39. The method of any one of aspects 26 to 38 further comprising administering an effective amount of GABA.

Aspect 40. The method of any one of aspects 26 to 39 further comprising administering an effective amount of serotonin or melatonin, or a pharmaceutically acceptable salt thereof.

Aspect 41. The method of any one of aspects 26 to 40 further comprising administering an effective amount of vasopressin or a vasopressin analog.

Aspect 42. The method of aspect 41, wherein the vasopressin analog is desmopressin, felypressin, ornipressin, selepressin, or terlipressin.

Aspect 43. The method of any one of aspects 26 to 42 further comprising administering an effective amount of a compound that affects neurotransmission.

Aspect 44. The method of aspect 43, wherein the compound that affects neurotransmission is a psychotropic drug, a neurotransmitter reuptake inhibitor, a compound that stimulates glutaminergic transmission, or a compound that affects cholinergic, serotonergic, vasopressin, oxytocin, or glutamate modulated neurotransmission.

Aspect 45. The method of any one of the aspects 26 to 44 further comprising administering an effective amount of a beta-adrenergic agonist, a psychopharmacologic drug, an anti-anxiety drug, or an antidepressant.

Aspect 46. The method of aspect 45 wherein the beta-adrenergic agonist is albuterol, levalbuterol, fenoterol, formoterol, isoproterenol, metaproterenol, salmeterol, terbutaline, clenbuterol, isoetarine, pirbuterol, procaterol, ritodrine, or epinephrine, or a pharmaceutically acceptable salt thereof.

Aspect 47. The method of aspect 45 wherein the psychopharmacologic drug is aripiprazole, pimavanserin, olanzapine, asenapine, clozapine, quetiapine, risperidone, lurasidone, cariprazine, paliperidone, brexpiprazole, iloperidone, ziprasidone, or balovaptan, or a pharmaceutically acceptable salt thereof.

Aspect 48. The method of aspect 45, wherein the anti-anxiety drug is a barbiturate, carbamate, antihistamine, opioids, benzodiazepines, beta blockers, tricyclic antidepressants, tetracyclic antidepressants, monoamine oxidase inhibitors (MAOIs) serotonin-norepinephrine reuptake inhibitors (SNRIs), mild tranquilizers, anticonvulsants, bupropion, or alpha blockers.

Aspect 49. The method of aspect 48, wherein the anti-anxiety drug is hydroxyzine, chlorpheniramine, diphenhydramine, hydrocodone, fentanyl, buprenorphine, alprazolam, clonazepam, diazepam, lorazepam, oxazepam, chlordiazepoxide propranolol, atenolol, imipramine, desipramine, nortriptyline, amitriptyline, doxepin, clomipramine, mirtazapine, trazodone, phenelzine, tranylcypromine, isocarboxazid, moclobemide, escitalopram, citalopram, venlafaxine, duloxetine, buspirone, valproate, pregabalin, gabapentin, bupropion, prazosin, or a pharmaceutically acceptable salt thereof.

Aspect 50. The method of aspect 45 wherein the antidepressant is fluoxetine, sertraline, citalopram, escitalopram, fluvoxamine, or paroxetine, or a pharmaceutically acceptable salt thereof.

What is claimed:

1. A method of treating generalized anxiety disorder (GAD), or panic disorder, in a subject in need thereof, comprising orally administering to the subject an effective amount of a tyrosine hydroxylase inhibitor.

2. The method of claim 1, for the treatment of generalized anxiety disorder (GAD).

3. The method of claim 1, for the treatment of panic disorder.

4. The method of claim 1, wherein said tyrosine hydroxylase inhibitor is selected from the group consisting of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate, H-D-tyrosine(tBu)-allyl ester hydrochloride, methyl (2R)-2 amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy]) benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyrosine methyl ester hydrochloride, H-3,5-diiodo-tyrosine methyl ester hydrochloride, H-D-tyrosine methyl ester hydrochloride, methyl D-tyrosinate hydrochloride, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-tyrosine (3,5-12)-OSu, Fmoc-tyrosine(3-$NO_2$)-OH, α-methyl-L-tyrosine, α-methyl-D-tyrosine, α-methyl-DL-tyrosine, $C_1$-$C_{12}$ alkyl ester salts of a-methyl-DL-tyrosine and α-methyl-DL-tyrosine methyl ester hydrochloride.

5. The method of claim 4, wherein the tyrosine hydroxylase inhibitor is α-methyl-DL-tyrosine.

6. The method of claim 1, wherein the method comprises administering 100-1200 mg of the tyrosine hydroxylase inhibitor daily.

7. The method of claim 6, wherein the method comprises administering 200-900 mg of the tyrosine hydroxylase inhibitor daily.

8. The method of claim 1, wherein the method comprises administering the tyrosine hydroxylase inhibitor in divided, substantially equal, doses.

9. The method of claim 1, further comprising administering an effective amount of gamma aminobutyric acid.

10. The method of claim 1, further comprising administering an effective amount of serotonin or melatonin, or a pharmaceutically acceptable salt thereof.

11. The method of claim 1, further comprising administering an effective amount of vasopressin or a vasopressin analog.

12. The method of claim 11, wherein the vasopressin analog is selected from the group consisting of desmopressin, felypressin, omipressin, selepressin, and terlipressin.

13. The method of claim 1, further comprising administering an effective amount of a compound that affects neurotransmission.

14. The method of claim 13, wherein the compound that affects neurotransmission is selected from the group consisting of i) a psychotropic drug; ii) a neurotransmitter reuptake inhibitor; iii) a compound that stimulates glutaminergic transmission; and iv) a compound that affects cholinergic, serotonergic, vasopressin, oxytocin, or glutamate modulated neurotransmission.

15. The method of claim 1, further comprising administering an effective amount of a beta-adrenergic agonist, a psychopharmacologic drug, an anti-anxiety drug, or an antidepressant.

16. The method of claim 15, wherein the beta-adrenergic agonist is selected from the group consisting of albuterol, levalbuterol, fenoterol, formoterol, isoproterenol, metaproterenol, salmeterol, terbutaline, clenbuterol, isoetarine, pirbuterol, procaterol, ritodrine, epinephrine, and a pharmaceutically acceptable salt thereof.

17. The method of claim 15, wherein the psychopharmacologic drug is selected from the group consisting of aripiprazole, pimavanserin, olanzapine, asenapine, clozapine, quetiapine, risperidone, lurasidone, cariprazine, paliperidone, brexpiprazole, iloperidone, ziprasidone, balovaptan, and a pharmaceutically acceptable salt thereof.

18. The method of claim 15, wherein the anti-anxiety drug is selected from the group consisting of a barbiturate, carbamate, antihistamine, opioid, benzodiazepine, beta blocker, tricyclic antidepressant, tetracyclic antidepressant, monoamine oxidase inhibitor (MAOI), serotonin-norepinephrine reuptake inhibitor (SNRT), mild tranquilizer, anticonvulsant, bupropion, and alpha blocker.

19. The method of claim 15, wherein the anti-anxiety drug is selected from the group consisting of hydroxyzine, chlorpheniramine, diphenhydramine, hydrocodone, fentanyl, buprenorphine, alprazolam, clonazepam, diazepam, lorazepam, oxazepam, chlordiazepoxide propranolol, atenolol, imipramine, desipramine, nortriptyline, amitriptyline, doxepin, clomipramine, mirtazapine, trazodone, phenelzine, tranylcypromine, isocarboxazid, moclobemide, escitalopram, citalopram, venlafaxine, duloxetine, buspirone, valproate, pregabalin, gabapentin, bupropion, prazosin, and a pharmaceutically acceptable salt thereof.

20. The method of claim 15, wherein the antidepressant is selected from the group consisting of fluoxetine, sertraline, citalopram, escitalopram, fluvoxamine, paroxetine, and a pharmaceutically acceptable salt thereof.

* * * * *